United States Patent [19]

Robinson et al.

[11] 4,059,573

[45] Nov. 22, 1977

[54] EXTRACTION OF N-BLOCKED AMINO ACIDS FROM AQUEOUS MEDIA

[75] Inventors: Colin Robinson, Grange-over-Sands; Derek Walker, Windermere, both of England

[73] Assignee: Glaxo Laboratories Limited, Greenford, England

[21] Appl. No.: 671,935

[22] Filed: Mar. 30, 1976

Related U.S. Application Data

[63] Continuation of Ser. No. 491,856, July 25, 1974, abandoned.

[30] Foreign Application Priority Data

Aug. 1, 1973 United Kingdom ............... 36498/73

[51] Int. Cl.² .......................................... C07C 103/52
[52] U.S. Cl. .......................... 260/112.5 R; 260/239.1; 544/20
[58] Field of Search ..................... 260/112.5 R, 239.1, 260/243 C; 195/29

[56] References Cited

U.S. PATENT DOCUMENTS

| 3,749,641 | 7/1973 | Takahashi et al. .................... 195/29 |
| 3,840,513 | 10/1974 | Umezawa et al. ............ 260/112.5 R |
| 3,840,516 | 10/1974 | Umezawa et al. ............ 260/112.5 R |
| 3,846,400 | 11/1974 | Umezawa et al. ............ 260/112.5 R |

*Primary Examiner*—Delbert R. Phillips
*Attorney, Agent, or Firm*—Bacon & Thomas

[57] ABSTRACT

N-blocked amino acids, particularly derived from natural sources such as fermentation liquors, are extractively esterified from aqueous media by treatment of the aqueous solution with a diazoalkane, e.g. diphenyldiazomethane, in the presence of a water-immiscible organic solvent. Useful applications of the process include the extractive esterification of N-blocked derivatives of cephalosporin C and desacetyl cephalosporin C from fermentation broths.

14 Claims, No Drawings

EXTRACTION OF N-BLOCKED AMINO ACIDS FROM AQUEOUS MEDIA

This is a continuation, of application Ser. No. 491,856, filed July 25, 1974 now abandoned.

This invention is concerned with a process for the extraction of N-blocked amino acids from aqueous solutions thereof, in particular from fermentation broths. It is to be understood that the term "N-blocked amino acid" as used in this specification embraces N-blocked peptides.

It is frequently required to isolate amino acids and N-blocked amino acids from aqueous solutions, for example from fermentation liquors and fermentor wastes or from solutions of substrates modified by the action of enzymes. Such isolations are often complicated by, for example, the comparative instability of many naturally-produced N-blocked amino acids in aqueous media and the fact that most fermentation and enzyme reactions yield the desired product only in dilute solution, so that complex and expensive isolation techniques are frequently necessitated.

Thus, for example, penicillin G [(3S,5R,6R)-2,2-dimethyl-6-phenylacetamidopenam-3-carboxylic acid] is unstable in the free acid form, especially in aqueous systems, and so requires special techniques for its efficient isolation from fermentation broths. These techniques may, for example, involve rapid extraction followed by selective and somewhat expensive purification steps to isolate an acceptably pure penicillin G product (e.g. a salt) of greater stability than the free acid. Alternatively the penicillin G may be isolated by sulphoxidation and separation of the resulting penicillin G sulphoxide. Cephalosporin C [(6R,7R)-3-acetoxymethyl-7-(R-5-amino-5-carboxypentanamido) ceph-3-em-4-carboxylic acid] is similarly difficult to separate from fermentation broths, by virtue of its amphoteric structure and hydrophilic nature. The isolation of fermentation-derived 3-hydroxymethyl cephalosporins such as desacetyl cephalosporin C [(6R,7R)-7-(R-5-amino-5-carboxypentanamido)-3-hydroxymethylceph-3-em-4-carboxylic acid] may likewise create problems because of the pronounced tendency of such compounds to undergo lactone formation by reaction of the hydroxy group in the 3-position side chain with the 4-carboxy group.

Illustrative of techniques which have been employed in the isolation of such N-blocked amino acids are the use of ion exchange resins and solvent extractions. The former technique, however, tends to be somewhat cumbersome and expensive in the treatment of dilute solutions on an industrial scale; the latter technique suffers the disadvantage that the acid to be isolated frequently exhibits comparatively poor solubility in organic solvents, so that solvent requirements and thus operating costs tend to be high.

We have now found, however, that efficient separation of N-blocked amino acids from their aqueous solutions can be achieved in a particularly simple manner by a process in which the acid is subjected to substantially simultaneous esterification and solvent extraction by reaction with a diazoalkane in the presence of a water-immiscible organic solvent, such processes hereinafter being referred to as extractive esterifications.

To the best of our knowledge, esterification reactions employing diazoalkanes in two phase aqueous organic solvent systems have not hitherto been reported. The fact that such reactions proceed smoothly and efficiently is somewhat surprising since one might expect other substances present which might be alkylated, e.g. water, to compete with the carboxyl group of the N-blocked amino acid in reacting with the diazoalkane. Such interference generally appears, however, to be minimal in the extractive esterification process of the invention.

Thus according to one aspect of the present invention we provide a process for extracting an N-blocked amino acid from an aqueous solution thereof which comprises treating the said solution with a diazoalkane in the presence of a water-immiscible organic solvent whereby a solution of an ester of the N-blocked amino acid in the organic solvent is produced.

Diazoalkane esterifying agents which may be used in this process include compounds of the general formula

wherein $R^1$ represents a hydrogen atom or an organic group and $R^2$ represents an organic group, or $R^1$ and $R^2$ together with the carbon atom to which they are attached form a cyclic organic group.

Suitable diazoalkanes thus include compounds of formula I wherein $R^1$ and/or $R^2$, which may be the same or different, are selected from carbocyclic aryl groups such an phenyl or naphthyl; 5- or 6-membered heterocylic rings containing one or more atoms of O,N and S (e.g. thien-2-yl, fur-2-yl or pyridin-2-yl); aralkyl groups (e.g. containing a monocyclic aryl group and 1–6 carbon atoms in the alkyl portion, such as benzyl); heterocyclic-substituted alkyl groups (e.g. containing 1–6 carbon atoms in the alkyl portion, such as thien-2-ylmethyl or fur-2-ylmethyl); alkyl groups (e.g. containing 1–6 carbon atoms, such as methyl, ethyl, n-propyl or isopropyl); cycloalkyl groups (e.g. containing 5–7 carbon atoms in the ring, such as cyclopentyl or cyclohexyl); unsaturated analogues of the above groups, for example carbocyclic or heterocyclic aralkenyl groups, lower (e.g. $C_{2-6}$) alkenyl groups (e.g. vinyl or allyl), and cycloalkenyl groups (e.g. containing 5–7 carbon atoms, such as cyclohexenyl or cyclopentadienyl); or any of the preceding groups substituted by one or more halogen atoms, cyano, nitro, alkyl, alkylsulphonyl or alkoxy groups, which last groups may, for example, contain 1–6 carbon atoms, as in, for example, methyl, ethyl, n-propyl, isopropyl, ethoxy, isopropoxy or methylsulphonyl.

Alternatively $R^1$ and $R^2$ may, together with the attached carbon atom, form a cyclic structure, e.g. a $C_{5-20}$ cycloaliphatic group, for example a cycloalkyl group (e.g. containing 5–7 carbon atoms, such as cyclopentyl or cyclohexyl) or a cycloalkenyl group (e.g. containing 5–7 carbon atoms, such as cyclohenxenyl or cyclopentadienyl); or a heterocyclic group containing at least one 5- or 6-membered ring which contains one or more heteroatoms selected from oxygen, nitrogen and sulphur (for example a monocyclic group such as pyranyl or piperidinyl).

Particularly useful diazoalkanes of formula I include compounds in which $R^1$ and $R^2$ are such that the resulting ester grouping Rhu $1R^2CH-$ is an aralkyl group containing 1 or 2 carbocyclic or heterocyclic aryl groups attached to the C-1 atom of a lower (e.g. $C_{1-6}$)

alkyl portion, e.g. benzyl, 1-phenylethyl, diphenylmethyl, naphthylphenylmethyl, di(thien-2-yl)methyl, pheny (thien-2-yl)methyl, or a substituted version of any of these groups, e.g. phenyl (o-toly)methyl or (p-methoxyphenyl)-phenylmethyl, since such ester groups may readily be cleaved at a subsequent stage in a reaction sequence. This list is not, however, intended to be exhaustive.

The N-blocked amino acid to be extracted may be represented by the formula Q.COOH, where Q is an organic group containing, for example, 1–50 carbon atoms and at least one blocked amino group, and may be a mono-, di-or polycarboxylic acid. Where a diazoalkane of formula I is employed, the resulting ester will correspond to the formula $Q.COOCHR^1R^2$, where $R^1$, where $R^2$ have the above-defined meanings.

Examples of N-blocked amino acids which may be extractively esterified in accordance with the invention include N-blocked derivatives of simple amino acids such as glycine, cysteine, methionine, aspartic acid, glutamic acid, phenylalanine, tryptophane and L-dopa, particularly from fermentation liquors; N-blocked peptides, particularly from fermentation liquors, plant and animal extracts, and complex aqueous reaction mixtures resulting from peptide syntheses, e.g. glutathione; and natural or semi-synthetic penicillin and cephalosporin compounds and related degradation products, e.g. penilloic acid or penicilloic acid, particularly from fermentation and other enzyme-catalysed processes.

The aqueous solution of the N-blocked amino acid to be extractively esterified may, if desired, contain a minor proportion (e.g. up to 30% v/v) of one or more cosolvents, e.g. water-miscible organic solvents such as lower alkanols (e.g. methanol), ketones (e.g. acetone), esters (e.g. ethyl acetate), N,N-disubstituted amides (e.g. dimethylacetamids) and ethers (e.g. cyclic ethers such as dioxan), for example to enhance the solubility of the N-blocked amino acid in the aqueous medium. Alternatively, in cases where the N-blocked amino acid exhibits particularly low solubility in water, the aqueous solution may take the form of slurry comprising a saturated aqueous solution of the N-blocked amino acid in contact and equilibrium with solid, undissolved N-blocked amino acid. References in this specification to aqueous solutions of N-blocked amino acids are therefore to be interpreted as embracing such slurries and aqueous organic solutions.

Illustrative of penicillins and cephalosporins which may be extractively esterified in accordance with the invention are compounds having the skeletal formula

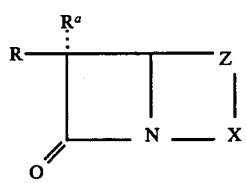

(II)

wherein Z is $>S$ or $>S\rightarrow C$; X is a divalent group selected from

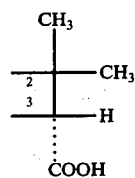

(a)

and

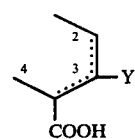

(b)

(where Y is methyl; substituted methyl e.g. —CH$_2$Y' where Y' is the residue of a nucleophile, including such groups as acetoxy, hydroxy or carbamoyloxy; or an unsaturated group such as vinyl or substituted vinyl and the dotted line between the 2-, 3- and 4-positions of (b) indicates that the compound may be a ceph-2-em or ceph-3-em compound; R is a blocked amino group, e.g. a carboxylic acylamido group (e.g. containing 1–20 carbon atoms) or a protonated amino group (NH$_3^+$); and R$^a$ is hydrogen or a lower (e.g. C$_{1-4}$) alkyl, alkoxy or alkylthio group, e.g. a methoxy group).

Where R is a carboxylic acylamido group, the acyl moiety thereof may be selected from the extensive lists of such acyl groups in the penicillin and cephalosporin literature. Specific acyl groups are illustrated in the accompanying list, which is not intended to be exhaustive:

i. R$^u$C$_n$H$_{2n}$CO— where R$^u$ is aryl (carbocyclic or heterocyclic), cycloalkyl, substituted aryl, substituted cycloalkly, cycloalkadienyl, or a non-aromatic heterocyclic or mesoionic group and $n$ is 0 or an integer from 1–4. Examples of this group include phenylacetyl; thien-2-and -3-ylacetyl, 3- and 4-isoxazolylacetyl both substituted or unsubstituted; pyridylacetyl, tetrazolyacetyl or a sydnoneacetyl group. Where $n$ is other than 0, especially when $n$ is 1, the α-carbon atom of the acyl group may be substituted by, for example, a hydroxy, esterified hydroxy (e.g. lower alkanoyloxy such as acetoxy), blocked amino (e.g. amino substituted by any of the blocking groups specified hereinafter), hydroxyimino, acyloxyimino (e.g. lower alkanoyloxyimino such as acetoxyimino or halo-substituted lower alkanoyloxyimino such as mono- or di-chloroacetoxyimino) or etherified oxyimino (e.g. lower alkoxyimino such as methoxyimino or t-butoxyimino, lower cycloalkyloxyimino such as cyclopentyloxyimino or aryloxyimino such as phenoxyimino) group; examples of α-substituted acyl groups of this type include 2-hydroxy-2-phenylacetyl, N-blocked 2-amino-2-phenylacetyl and 2-(fur-2-yl)-2-hydroxyiminoacetyl.

ii. C$_n$H$_{2n+1}$CO—where $n$ is 0 or an integer from 1–14 7. The alkyl group may be straight or branched and may be substituted by e.g. a cyano group, a carboxy group, an alkoxycarbonyl group, a hydroxy group, a blocked amino group or a carboxycarbonyl group (—CO.-COOH) or any such group in which the functional group is blocked. Examples of such groups include formyl, glutaroyl, and N-blocked (e.g. N-ethoxycarbonyl) R-5-amino-5-carboxypentanoyl.

iii.

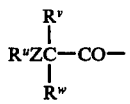

where $R^u$ has the meaning defined under (i) and in addition may be benzyl, and $R^v$ and $R^w$ which may be the same of different each represent hydrogen, phenyl, benzyl, phenethyl, or lower alkyl and Z is an oxygen or sulphur atom. Examples of this group include phenoxyacetyl or pyridylthioacetyl.

It should be appreciated that skeletal formula II includes within its structure compounds not specifically embraced by groups (a) and (b), e.g. 2-acetoxymethylpenicillins and 2-methyl and 2-methylene cephalosporins.

Compounds of formula (IIb) wherein Y' is the residue of a nucleophile may be prepared by reacting the compound of formula (IIb) where Y' is acetoxy with a nucleophile, for example pyridine or other tertiary amine as described in British Pat. No. 912,541; a sulphur-linking, nitrogen-linking or inorganic nucleophile as described in British Pat. No. 1,012,943; a sulphur-linking nucleophile as described in British Pat. No. 1,059,562; a nitrogen-linking nucleophile as described in British Pat. Nos. 1,030,630, 1,082,943 and 1,082,962; or a sulphur-linking mucleophile as described in British Pat. Nos. 1,101,423 and 1,206,305. This list is not limiting and is given purely by way of illustration.

Compounds of formula (IIb) where Y' is a hydroxy group may be prepared by the methods described in British Pat. No. 1,121,308; compounds in which Y' is a carbamoyloxy group are described in Belgian Pat. No. 764,160.

Where Y in formula (IIb) is a methyl group the compound may be prepared by the method described in British Pat. No. 957,569.

As indicated above, the amino acid to be separated using the process of the invention should be in N-blocked form, since this generally enhances the solubility of the resulting ester in the organic solvent and thus improves the efficiency of the extraction. Accordingly, where it is desired to extractively esterify an acid containing one or more free amino groups, e.g. a simple amino acid or a penicillin or cephalosporin acid containing an amino group in the 6- or 7- position side chain, such groups should be blocked prior to esterification by protonation or by substitution with a blocking group.

Where protonation is used to block an amino group, protonation is preferably effected using a strong acid which confers some lipid solubility on the resulting protonated amino acid. Suitable strong acids for this purpose include aromatic sulphonic acids, for example lower alkyl-substituted benzene sulphonic acids (e.g. p-toluene sulphonic acid) and naphthalene sulphonic acids.

N-blocking groups which may be used to protect amino groups by substitution may be mono- or divalent, suitable groups including acyl groups, for example lower alkanoyl such as acetyl, substituted lower alkanoyl, e.g. lower haloalkanoyl such as chloroacetyl, aryl-lower alkanoyl such as phenylacetyl, and aroyl such as benzoyl or phthaloyl; lower alkoxycarbonyl groups such as ethoxycarbonyl, isobutyloxycarbonyl or t-butyloxycarbonyl and substituted lower alkoxycarbonyl groups, e.g. lower haloalkoxycarbonyl such as 2,2,2-trichloroethoxycarbonyl; aryl-lower alkoxycarbonyl groups such as benzyloxycarbonyl; sulphonyl groups, for example lower alkylsulphonyl such as methanesulphonyl and arylsulphonyl such as benzenesulphonyl or p-toluenesulphonyl; ylidene groups formed by reaction with aldehydes and ketones which form Schiffs bases, for example benzaldehyde, salicaldehyde or acetcacetic ester; and divalent groups such that the nitrogen atom forms part of a dihydropyridine ring, such protecting groups being obtained by, for example, reaction with formaldehyde and a β-ketoester, e.g. acetoacetic ester, as described in our Belgian Pat. No. 771,694.

In general such N-blocking groups may be introduced by methods known per se, e.g. by reaction of the amino acid with an acyl halide where an acyl N-blocking group is to be introduced. The N-blocking group is desirably introduced at a pH above the isoelectric point of the amino acid, preferably at a pH in the range 6–10, and the reaction temperature is advantageously comparatively low in order to minimise decomposition of the acid. Other groups, e.g. hydroxyl or thiol groups, present in the amino acid may, if desired, also be blocked prior to the extractive esterification.

The water immiscible solvent employed in the extractive esterification should be substantially inert to the reaction conditions and should be capable of at least partially dissolving the esterified N-blocked amino acid, so that the nature of the solvent will depend on the particular N-blocked amino acid to be extracted. In general, organic solvents which may be used include chlorinated hydrocarbons, for example methylene chloride, chloroform or chlorobenzene; aliphatic and aromatic esters, for example ethyl acetate, butyl acetate or ethyl benzoate; water-immiscible ketones, for example methyl ethyl ketone or methyl isobutyl ketone; aliphatic and aromatic hydrocarbons, for example benzene; and alcohols, for example water-immiscible lower alkanols such as n-butanol. Mixtures of the above solvents may also be used.

The extractive esterification is conveniently effected by adding a solution of the diazoalkane in the chosen organic solvent to the aqueous solution containing the N-blocked amino acid, since in this way substantially simultaneous occurence of esterification of the N-blocked amino acid and extraction into the organic solvent may be achieved, enhancing the efficiency of the process. Alternative modes of addition are possible, however, although lower yields of isolated N-blocked amino acid ester may result. Thus, for example, the aqueous solution may first be treated with a water-immiscible organic solvent to effect at least partial extraction of the n-blocked amino acid, whereafter the diazoalkane may be added to promote the desired esterification.

The extractive esterification of the N-blocked amino acid may if desired be conducted in the presence of one or more further acids. The presence of a strong acid having a pKa less than that of the N-blocked amino acid, e.g. a mineral acid such as sulphuric acid, orthophosphoric acid or perchloric acid, may not interfere with the extractive esterification; thus the diazoalkane in many instances tends predominantly to react with and esterify the weaker acid present, i.e. to react preferentially with the N-blocked amino acid. The amount of any strong acid added to the reaction system will be governed at least in part by the stability of the components of the system under acid conditions; thus, for example, the pH of the reaction solution should desirably not be reduced to below about 1.5 since side reactions involving decomposition of the diazoalkane tend to predominate at such low pH values, and in general we prefer to employ solutions having a pH in excess of about 1.7, for example in the range 2.0 –4.0.

The extractive esterification may in certain circumstances be conducted in the presence of acids which are weaker than the N-blocked amino acid. Thus, for example, penicillin V and N-blocked cephalosporin C may be selectively extractively esterified in the presence of the weaker acids phenoxyacetic acid and acetic acid respectively. While we do not wish to be bound by theoretical considerations it is believed that the solubility of the N-blocked amino acid in the water-immiscible organic solvent is an important contributory factor in such extractive esterifications, the rate of esterification and the selectivity of the process improving as the solubility of the N-blocked amino acid in the organic solvent increases.

It is surprising that successful extractive esterifications can be conducted under acid conditions using diazoalkane esterifying agents since it is known that the stability of diazoalkanes is comparatively low in acid media.

The order of addition of the diazoalkane, organic solvent and any added strong acid to the aqueous N-blocked amino acid will in general depend on the nature of the amino acid substrate. Thus the mode of addition is not critical in cases where the N-blocked amino acid is acid-stable, but where an acid-sensitive substrate such as penicillin G or N-blocked desacetyl cephalosporin C is to be extracted it is desirable to add the strong acid after the diazoalkane and organic solvent since we have found that under such conditions esterification of the N-blocked amino acid by the diazoalkane and consequent stabilisation of the amino acid as its ester proceeds very rapidly, so that minimal acid-induced decomposition or other transformation of the amino acid occurs. Using this mode of addition, aqueous solutions of acid-sensitive N-blocked amino acids may be stabilised up to the time of extractive esterification by maintaining a pH at which degradation of the N-blocked amino acid is minimised or obviated, e.g. a neutral or basic pH. Reduction of the pH by acidification of the solution after addition of the diazoalkane and organic solvent then permits rapid esterification of the N-blocked amino acid by the diazoalkane.

In many cases we prefer to employ an excess of the diazoalkane in the extractive esterification, the precise amount depending on the nature of the diazoalkane and the N-blocked amino acid. Typically the amount of diazoalkane required will be about 1.0 –1.5 moles per equivalent of acid. Thus, for example, when it is desired to extract a dibasic acid, e.g. a cephalosporin diacid, it is convenient to use 2-3 moles of the diazoalkane, e.g. about 2.1 moles per mole of the dibasic acid.

The extractive esterification process according to the invention may be effected at, for example, a temperature in the range −10° to +100° C, e.g. 0°–50° C, advantageously at room temperature, and may be monitored by, for example, measuring the evolution of nitrogen from the reaction system, this giving a virtually quantitative indication of the extent of decomposition of the diazoalkane, or by spectroscopic techniques, e.g. following the formation of ester linkages by I.R. spectroscopy or the decomposition of dizao groups as evidenced by loss of I.R. and U.V. or visible absorption.

After completion of the extractive esterification the N-blocked amino acid ester may be isolated using, for example, conventional techniques. Thus the organic solvent may be separated from the aqueous solution, purified e.g. by washing, and the solvent evaporated to yield the desired ester. Alternatively the organic solution may be subjected to further reaction without intermediate separation of the N-blocked amino acid ester. Thus, for example, an extracted penicillin ester may be directly converted to its sulphoxide for use in a ring expansion reaction.

As indicated above, the extractive esterification process of the invention is of particular value in the isolation of naturally-produced amino acids and N-blocked amino acids, especially penicillins and cephalosporins, from fermentation liquors. Compounds which may be extractively esterified using the process of the invention thus include naturally occuring penicillins such as penicillin G, penicillin V and their hydroxylated and 6α-methoxylated analogues, and naturally occuring cephalosporins such as cephalosporin C, desacetyl cephalosporin C, desacetoxy cephalosporin C, 3-carbamoyloxymethyl cephalosporins and 7α-methoxylated analogues of these compounds, wherein any free amino groups have first been blocked. The process may also be used with advantage in the isolation of N-blocked amino acids obtained from enzymic reactions, for example (6R,7R)-3-acetoxymethyl-7-(4-carboxybutanamido)ceph-3-em-4-carboxylic acid, which may be prepared by enzymic oxidation of cephalosporin C and has hitherto been somewhat difficult to isolate by, for example, solvent extraction because of its low solubility in water-immiscible organic solvents.

Particularly important uses of the process of the invention include the extractive esterification of cephalosporin C and 3-hydroxymethyl cephalosporins, especially desacetyl cephalosporin C. 3-Hydroxymethyl cephalosporins are difficult to isolate using conventional techniques by virtue of their pronounced tendency to lactone formation, particularly under acid conditions. In the case of desacetyl cephalosporin C, the resulting lactone is a stable compound having little antibiotic activity and no value as a starting material in the preparation of semisynthetic cephalosporin antibiotics. Carboxylate salts of 3-hydroxymethyl cephalosporins are, however, substantially resistant to such lactone formation so that efficient isolation in accordance with the invention may be achieved by conducting any preliminary treatment e.g. N-blocking, of the aqueous 3-hydroxymethyl cephalosporin solution at basic pH, thereafter adding a diazoalkane and water-immiscible organic solvent, followed by a strong acid, as described hereinbefore, to promote extractive esterification.

In the case of extractive esterification of desacetyl cephalosporin C, for example, the necessary N-blocking may be carried out under basic conditions, for example by reaction with an appropriate acylating agent (e.g. benzoyl chloride or an alkyl haloformate such as ethyl chloroformate) in the presence of excess base (e.g. an alkali metal hydroxide such as sodium hydroxide or a buffer such as potassium phosphate). Thereafter, a solution of the diazoalkane (e.g. diphenyldiazomethane) in a suitable solvent may be added, if desired after extraction at substantially neutral pH (e.g. in the range pH 5–8) to remove by-products of the N-blocking reaction, and the solution acidified, for example to a pH in the range 2–4 (e.g. to about pH 3.5) with a strong acid (e.g. a mineral acid such as sulphuric or orthophosphoric acid) to promote the extractive esterification.

The aqueous desacetyl cephalosporin C starting solution in extractions such as that described above is desirably substantially free of cephalosporin C.

The ability to extract desacetyl cephalosporin C in an efficient and economical manner is of considerable value, since typical cephalosporin C fermentation broths obtained by fermentation of *Cephalosporium acremonium* contain a significant proportion of desacetyl cephalosporin C, the majority of which is normally lost in the isolation of cephalosporin C by conventional techniques. This wastage of a potentially valuable starting material for the manufacture of semi-synthetic cephalosporins is clearly undesirable and it will be appreciated that significant economic advantages will accrue if the desacetyl cephalosporin C content of a fermentation broth is isolated in addition to the cephalosporin C content.

The extraction esterification process of the invention may be employed in a number of ways in the treatment of cephalosporin fermentation broths, depending on the desired product. Thus, for example, it may be convenient initially to treat the broth, if desired after preliminary treatment such as filtration, with an esterase serving to deacetylate the cephalosporin C content of the broth, advantageously an esterase produced by culturing a yeast microorganism or a mutant thereof of the genus Rhodotorula, e.g. a microorganism of the species *Rhodotorula rubra*, and thereafter to subject the reaction product to an N-blocking reaction (e.g. by treatment with benzoyl chloride or ethyl chlorformate under basic conditions) and extractive esterification to yield a substantially pure N-blocked desacetyl cephalosporin C ester derivative. Alternatively the cephalosporin C and desacetyl cephalosporin C content of broth may initially be subjected to an N-blocking reaction and extractive esterification to give a mixture of N-blocked cephalosporin C and desacetyl cephalosporin C ester derivatives, which may then be treated with an acetylating agent (e.g. acetyl chloride) to acetylate the N-blocked desacetyl cephalosporin C ester content of the mixture and thereby yield a product comprising a substantially pure N-blocked cephalosporin C ester derivative.

The diazoalkanes used as esterifying agents in the process of the present invention may conveniently be prepared as described in our Belgian Pat. No. 802,112, by oxidation of the corresponding hydrazone using an organic peracid, periodic acid, a hypohalous acid or hypohalite salt or ester, chromic acid, chlorine, bromine or a source of positive halogen such as an N-halo-amide or imide. Peracetic acid is a particularly preferred oxidising agent for this purpose. The oxidation is preferably conducted in the presence of a base and advantageously also an oxidation catalyst, e.g. iodine.

The following non-limitative examples serve to illustrate the invention. All temperatures are in ° C.

EXAMPLE 1

(6R,7R)-7-(R-5-Benzoylamino-5-carboxypentanamido)-3-hydroxymethylceph-3-em-4-carboxylic acid bis diphenylmethyl ester To a solution of potassium (6R,7R)-7-(R-5-amino-5-carboxypentanamido)-3-hydroxymethylceph-3-em-4-carboxylate (70% purity, 6.0g, 10 mM) in water (150 ml) was added a mixture of benzoyl chloride (3.5 ml, 30 mM) and acetone (5 ml). The mixture was stirred for 1.5 hours at room temperature, the pH being maintained at 8.5 by addition of 50% potassium phosphate. The pH was adjusted to 5.0 with orthophosphoric acid and the solution extracted with chloroform (100 ml) to remove benzoic acid and benzoyl chloride. Ethyl acetate (90 ml) containing diphenyldiazomethane (5g, 26 mM), dichloromethane (50 ml) and ethanol (10 ml) were added to the aqueous solution and the mixture stirred for 45 minutes during which time the pH was adjusted to 2.0 with orthophosphoric acid.

After separation the solvent layer was washed with 5% sodium bicarbonate solution (100 ml) and water (100 ml). The solvent was removed in vacuo and the gum dissolved in isopropanol (25 ml) at 30°. Petroleum ether (b.p. 30°–40°, 10 ml) was added and the solution cooled to −5°. The product was washed with petroleum either (15 ml) and dried in vacuo at room temperature to give the title product (10.5g).

Thin layer chromatography on silica gel GF254 plates using chloroform:acetone:acetic acid (80:20:2) as irrigant indicated that the product was mainly the title compound with traces of impurity.

EXAMPLE 2

Diphenylmethyl (3S, 5R, 6R)-2,2-dimethyl-6-phenoxyacetamidopenam-3-carboxylate 1-oxide To a solution of potassium (3S, 5R, 6R)-2,2-dimethyl-6-phenoxyacetamidopenam-3-carboxylate (7.8 g, 20 mM) in water (100 ml) was added a solution of diphenyldiazomethane (4 g, 20 mM) in dichloromethane (75 ml). The mixture was stirred for 15 minutes at 10° during which time the pH was adjusted to 3.5 by addition of orthophosphoric acid. The mixture was separated and the solvent layer washed with water (100 ml), 5% sodium bicarbonate solution (100 ml) and water (100 ml). Peracetic acid (18.5 ml, 37% w/v) was added to the solvent over 15 minutes at 10° with 30 minutes extra stirring. The solvent was washed with water (100 ml), 5% sodium bicarbonate soluion (100 ml) and water (100 ml). The solvent was removed in vacuo and the title product crystallised from hot isopropanol (9.1 g).

IR and NMR data confirmed the structure as that of the title compound.

EXAMPLE 3

(6R, 7R)-3-Acetoxymethyl-7-(R-5-benzoylamino-5-carboxypentanamido)-ceph-3-em-4-carboxylic acid bis diphenylemthyl ester To a solution of (6R, 7R)-3-acetoxymethyl-7-(R-5-benzoylamino-5-carboxypentanamido)ceph-3-em-4-carboxylic acid (4.8 g, 10 mM) in water (100 ml) was added a solution of diphenyldiazomethane (4 g, 20 mM) in dichloromethane (75 ml), ethyl acetate (25 ml) and ethanol (10 ml). The mixture was stirred for 30 minutes at room temperature during which time the pH was adjusted to 2.0 with orthophosphoric acid. After separation the solvent was washed with 5% sodium bicarbonate solution (100 ml) and water (100 ml). After drying, the solvent was removed in vacuo and the gum treated with petroleum ether (40°–60°) to give the title compound, (6.0 g).

IR and NMR data confirmed the structure as that of the title compound.

EXAMPLE 4

(6R, 7R)-7-(R-5-Carboxy-5-isobutyloxycarbonylaminopentanamido)-3-hydroxymethylceph-3-em-4-carboxylic acid bis diphenylmethyl ester Isobutylchloroformate (50 ml, 375 mM) was added over 1 hour to a solution of potassium (6R, 7R)-7-(R-5-amino-5-carboxypentanamido)-3-hydroxymethylceph-3-em-4-carboxylate (34.4 g, 60 mM) in water (350 ml) at pH 7.8–8.0 and 5°. The mixture was stirred for a further 30 minutes maintaining a temperature of 5° and a pH of 7.8–8.0. The solution was extracted with chloroform (250 ml) at pH 5.0. A solution of diphenyldiazomethane (25 g, 126 mM) in dichloromethane (250 ml), ethyl acetate (100 ml) and ethanol (30 ml) was added to the aqueous solution. The mixture was stirred for 30 minutes at 15° C during which time the pH was adjusted to 2.0 with orthophosphoric acid. After separation, the solvent was washed with 5% sodium bicarbonate solution (2 × 100 ml) and water (100 ml). After drying the solvent was removed in vacuo and the gum treated with petroleum ether (40°–60°) to give the title compound (45.5 g).

IR and NMR data confirmed the structure as that of the title compound.

EXAMPLE 5

(6R, 7R)-7-(R-5-Benzenesulphonylamino-5-carboxypentanamido)-3-hydroxymethylceph-3-em-4-carboxylic acid bis diphenylmethyl ester To a solution of potassium (6R, 7R)-7-(R-5-amino-5-carboxypentanamido)-3-hydroxymethylceph-3-em-4-carboxylate (4.1 g, 10 mM) in water (120 ml) containing sodium bicarbonate (9g) was added a solution of benzenesulphonyl chloride (2 ml, 15.7mM) in acetone (15 ml) over 30 minutes. The reaction temperature (10°) and solution pH (7.8–8.0) were maintained for a further 90 minutes. The solution was extracted with chloroform (2 × 100 ml) at pH 5.0. A solution of diphenyldiazomethane (6.0 g, 30 mM) in dichloromethane (80 ml), ethyl acetate (150 ml) and ethanol (20 ml) was added to the aqueous solution and the mixture stirred for 30 minutes during which time the pH was adjusted to 2.0 with orthophosphoric acid. After separation, the solvent was washed with 5% sodium bicarbonate solution (2 × 100 ml) and water (100 ml). After drying, the solvent was removed in vacuo and the gum treated with petroleum ether (40°–60°) to give the title compound (5.8 g).

TLC and IR data indicated the structure to be that of the title compound.

EXAMPLE 6

Diphenylmethyl (6R, 7R)-3-hydroxymethyl-7-(thien-2-ylacetamido)ceph-3-em-4-carboxylate To a solution of potassium (6R, 7R)-3-hydroxymethyl-7-(thien-2-ylacetamido)caph-3-em-4-carboxylate (4.0 g, 10 mM) in water (100 ml) was added a solution of diphenyldiazomethane (2.0 g, 10 mM) in dichloromethane (75 ml) and ethanol (10 ml). The mixture was stirred for 25 minutes, during which time the pH was adjusted to 2.0 with orthophosphoric acid. After separation, the solvent was washed with water (100 ml), 5% sodium bicarbonate solution (2 × 100 ml) and water (100 ml). After drying the solvent was removed in vacuo and the gum treated with petroleum ether (40°–60°) to give the title compound (5.15 g).

IR and NMR data confirmed the structure as that of the title compound.

EXAMPLE 7

(6R, 7R)-3-Acetoxymethyl-7-(4-carboxybutanamido)ceph-3-em-4-carboxylic acid bis diphenylmethyl ester To a slurry of (6R, 7R)-3-acetoxymethyl-7-(4-carboxybutanamido)ceph-3-em-4-carboxylic acid (0.24 g, 0.575 mM) was added diphenyldiazomethane (0.3 g, 1.5 mM) in dichloromethane (15 ml). The mixture was stirred for 15 minutes during which time the pH was adjusted to 2.0 with orthophosphoric acid. The mixture was then stirred for a further 75 minutes at ambient temperature. After separation the solvent was washed with 5% sodium bicarbonate solution (2 × 25 ml) and water (25 ml). After drying, the solvent was removed in vacuo and the gum treated with petroleum ether (40°–60°) to give the title compound (0.38 g).

IR and NMR data confirmed the structure as that of the title compound.

EXAMPLE 8

(6R, 7R)-7-(R-5-Isobutyloxycarbonylamino-5-carboxypentanamido)-3-hydroxymethylceph-3-em-4-carboxylic acid bis phenyl (o-tolyl) methyl ester To a solution of potassium (6R, 7R)-7-(R-5-amino-5-carboxypentanamido)-3-hydroxymethylceph-3-em-4-carboxylate (67.1% purity, 11.2 g, 20 mM) in water (100 ml) was added isobutyl chloroformate (16 ml, 120 mM) over 1 hour at 10° and pH 7.8–8.0. The mixture was stirred for a further 30 minutes maintaining a pH of 7.8–8.0. The pH was adjusted to 5.0 with orthophosphoric acid and extracted with chloroform (2 × 100 ml). A solution of (o-tolyl) phenyldiazomethane (4.2 g, 40 mM) in a mixture of dichloromethane (120 ml), ethyl acetate (60 ml) and ethanol (20 ml) was added to the aqueous solution. The mixture was stirred for 45 minutes during which time the pH was adjusted to 2.0 with orthophosphoric acid. After separation the solvent was washed with water (100 ml), 5% sodium bicarbonate solution (2 × 100 ml) and water (100 ml). After drying, the solvent was removed in vacuo and the gum treated with petroleum ether (40°–60°) to give the title compound (16.9 g).

EXAMPLE 9

(6R, 7R)-7-[R-5-Carboxy-5-(3,5-diethoxycarbonyl-2,6-dimethyl-1,4-dihydropyridin-1-yl) pentanamido]-3-hydroxymethylceph-3-em-4-carboxylic acid bis diphenylmethyl ester To a solution of potassium (6R, 7R)-7-(R-5-amino-5-carboxypentanamido)-3-hydroxymethylceph-3-em-4-carboxylate (70% purity, 12 g, 20 mM) was added 37% formaldehyde solution (18.7 ml, 249 mM) and ethyl acetoacetate (25.2 ml, 199 mM) separately over 1 hour at 5°. The solution pH was maintained at 7.0 by addition of 25% potassium phosphate solution. After a further 30 minutes stirring, the solution was extracted with dichloromethane (200 ml). Dichloromethane (150 ml) containing diphenyldiazomethane (10 g, 52mM) was added to the aqueous solution and the mixture sirred for 45 minutes during which time the pH was adjusted to 2.0 with orthophosphoric acid. After separation, the solvent layer was washed with water (200 ml), 5% sodium bicarbonate solution (200 ml) and water (200 ml). After drying over magnesium sulphate, the solution was concentrated in vacuo to a volume of 75 ml to give a solution of the title compound.

EXAMPLE 10

(6R, 7S)-7-(R-5-Benzyloxycarbonylamino-5-carboxypentanamido)-3-carbamoyloxymethyl-7-methoxyceph-3-em-4-carboxylic acid bis diphenylmethyl ester Benzyl chloroformate (3.5 ml) was added over 1 hour to a stirred solution of the monoammonium salt of (6R, 7S)-7-(R-5-amino-5-carboxypentanamido)-3-carbamoyloxymethyl-7-methoxyceph-3-em-4-carboxylic acid (approx. 5% purity, 4 g) in water (80 ml) containing sodium bicarbonate (6 g) at 10°. The pH was maintained at 7.8-8 throughout by the addition of N sodium hydroxide. The mixture was stirred at 10° and pH 7.8-8 for a further 90 minutes. The pH was adjusted to 5 with orthophosphoric acid and the solution washed with chlorofrom (2 × 100 ml). To the aqueous phase was added ethyl acetate (50 ml), ethanol (10 ml) and a solution of diphenyldiazomethane in methylene chloride (50 ml, approx. 0.2 M). The mixture was stirred at 15° for 45 minutes during which time the pH was adjusted to 2 with orthophosphoric acid. After separation, the organic phase was washed with 5% aqueous sodium bicarbonate (2 × 75 ml) and with water (100 ml), dried (Na$_2$SO$_4$) and evaporated to a gum (2.9 g). Purification by column chromatography (silica gel; ethyl acetate and chloroform) followed by preparative thin layer chromatography (silica gel; chloroform and methanol) gave the title compound as a white foam (260 mg), IR, NMR, UV and microanalysis data confirmed the structure as that of the title compound.

EXAMPLE 11

(6R, 7S)-7-[R-5-Carboxy-5-(2,2,2-trichloroethoxycarbonylamino)-pentanamido]-3-carbamoyloxymethyl-7-methoxyceph-3-em-4-carboxylic acid bis diphenylmethyl ester 2,2,2Trichloroethyl chloroformate (3 ml) was added over 1 hour to a stirred solution of the monoammonium salt of (6R, 7S)-7-(R-5-amino-5-carboxypentanamido)-3-carbamoyloxymethyl-7-methoxyceph-3-em-4-carboxylic acid (approx. 5% purity, 4 g) in water (80 ml) containing sodium bicarbonate (6 g) at 10°. The pH was maintained at 7.8-8 throughout by the addition of N sodium hydroxide. The mixture was stirred at 10° and pH 7.8-8 for a further 90 minutes. The pH was adjusted to 5 with orthophosphoric acid and the solution washed with chloroform (2 × 100 ml). To the aqueous phase was added ethyl acetate (50 ml), ethanol (10 ml) and a solution of diphenyldiazomethane in methylene chloride (50 ml, approx. 0.2 M). The mixture was stirred at 15° for 30 minutes during which time the pH was adjusted to 2 with orthosphoric acid. After separation, the organic layer was washed with 5% aqueous sodium bicarbonate solution (2 × 80 ml) and with water (100 ml), dried (Na$_2$SO$_4$) and evaporated to give a gum (2.8 g). Purification by column chromatography (silica gel; chloroform and ethyl acetate) followed by preparative thin layer chromatography (silica gel; chloroform and methanol) gave the title compound as a white foam (410 mg). IR, NMR, UV and microanalysis data confirmed the structure as that of the title compound.

EXAMPLE 12

(6R, 7S)-7-(R-5-Benzoylamino-5-carboxypentanamido)-3-carbamoyloxymethyl-7-methoxyceph-3-em-4-carboxylic acid bis diphenylmethyl ester A solution of the monoammonium salt of (6R, 7S)-7-(R-5-amino-5-carboxypentanamido)-b 3-carbamoyloxymethyl-7-methoxyceph-3-em-4-carboxylic acid (approx. 8% purity, 5 g, approx. 0.85 mM) in water (100 ml) was adjusted to pH 8.3 with 50% potassium phosphate solution. A solution of benzoyl chloride (3 ml, 26 mM) in acetone (5 ml) was added and the mixture stirred at room temperature for 1.5 hours, the pH being maintained at 8.3 by the addition of 50% potassium phosphate. The pH was adjusted to 5 with phosphoric acid and the solution washed with chloroform (100 ml). To the aqueous phase was added ethyl acetate (90 ml), ethanol (10 ml) and a solution of diphenyldiazomethane in methylene chloride (50 ml, approx. 0.2 M). The mixture was stirred for 45 minutes during which the pH was adjusted to 2 with orthophosphoric acid. After separation, the organic layer was washed with 5% aqueous sodium bicarbonate (100 ml) and with water (100 ml), dried (Na$_2$SO$_4$) and evaporated to a gum (2.6 g). Purification by preparative thin layer chromatography (silica gel; chloroform and ethyl acetate) gave the title compound as a white foam (554 mg). IR, NMR, UV and microanalysis data confirmed the structure as that of the title compound.

EXAMPLE 13

(6R, 7R)-7-[R-5-Carboxy-5-(2,2,2-trichloroethoxycarbonylamino) pentanamido]-3-hydroxymethylceph-3-em-4-carboxylic acid bis diphenylmethyl ester 2,2,2-Trichloroethyl chloroformate (5ml, 37 mM) was added to a solution of potassium (6R, 7R)-7-(R-5-amino-5-carboxypentanamido)-3-hydroxymethylceph-3-em-4-carboxylate (20 mM) in water (100 ml). The solution pH was maintained at 7.5-8.0 for 30 minutes using 10% w/v sodium hydroxide solution. The solution was then extracted with dichloromethane (50 ml) at pH 5.0. A solution of diphenyldiazomethane (8.5 g, 44 mM) in dichloromethane (150 ml) was added to the aqueous phase and the pH adjusted to 3.5 using 10% v/v sulphuric acid over 15 minutes. After separation the solvent was washed with water (3 × 150 ml). The solvent was removed in vacuo to give the title compound (20.5 g).

IR and NMR data confirmed the structure as that of the title compound.

EXAMPLE 14

(6R, 7R)-7-[R-5-Carboxy-5-(2,2,2-trichloroethoxycarbonylamino) pentanamido]-3-hydroxymethylceph-3-em-4-carboxylic acid bis naphthylphenylmethyl ester The process of Example 13 as repeated, except that a solution of naphthylphenyldiazomethane (approx. 44 mM) in dichloromethane (150 ml) was used in place of the solution of diphenyldiazomethane in dichloromethane, to give the title compound (23.3 g).

IR and NMR data confirmed the structure as that of the title compound.

EXAMPLE 15

(6R, 7R)-7-[R-5-Carboxy-5-(2,2,2-trichloroethoxycarbonylamino) pentanamido]-3-hydroxymethylceph-3-em-4-carboxylic acid bis (p-methoxyphenyl)phenylmethyl ester The process of Example 13 was repeated, except that a solution of (p-methoxyphenyl) phenyldiazomethane (approx: 44 mM) in dichloromethane (150 ml) was used in place of the solution of diphenyldiazomethane in dichloromethane, to give the title compound (6.4 g).

IR and NMR data confirmed the structure as that of the title compound.

EXAMPLE 16

(6R,7R)-7-[R-5-Carboxy-5-(2,2,2-trichloroethoxycarbonylamino) pentanamido]-3-hydroxymethylceph-3-em-4-carboxylic acid bis 1-phenylethyl ester The process of Example 13 was repeated, except that a solution of 1-phenyldiazoethane (approx. 44 mM) in dichloromethane (150 ml) was used in place of the solution of diphenyldiazomethane in dichloromethane, to give the title compound (18.6 g).

IR and NMR data confirmed the structure as that of the title compound.

EXAMPLE 17

(6R,7R)-7-(R-5-Carboxy-5-ethoxycarbonylaminopentanamido)-3-hydroxymethylceph-3-em-4-carboxylic acid bis diphenylmethyl ester.

The process of Example 13 was repeated, except that ethyl chloroformate (5 ml, 52 mM) was used in place of the 2,2,2-trichloroethyl chloroformate, to give the title compound (15.7 g).

IR and NMR data confirmed the structure as that of the title compound.

EXAMPLE 18

Diphenylmethyl (6R,7R)-3-acetoxymethyl-7-(thien-2-ylacetamido)ceph-3-em-4-carboxylate To a solution of sodium (6R, 7R)-3-acetoxymethyl-7-(thien-2-ylacetamido)ceph-3-em-4-carboxylate (4.2 g, 10 mM) in water (50 ml) was added dichloromethane (30 ml) containing diphenyldiazomethane (2.1 g, 11 mM). The solution pH was adjusted to 3.0 over 15 minutes using 10% v/v sulphuric acid. The mixture was separated and the solvent phase washed with water (4 × 50 ml). The solvent was removed in vacuo to give the title compound (6.96 g).

IR and MNR data confirmed the structure as that of the title compound.

EXAMPLE 19

Diphenylmethyl (5R,6R)-2,2-dimethyl-6-phenoxyacetamidopenam-3-carboxylate

To a solution of potassium (5R,6R)-2,2-dimethyl-6-phenoxyacetamidopenam-3-carboxylate (10 g, 25.7 mM) and phenoxyacetic acid (2 g, 13.1 mM) in water (100 ml) was added a solution of diphenyldiazomethane (5.2 g, 27 mM) in dichloromethane (100 ml). The pH was adjusted to 4.0 and the mixture stirred for 10 minutes. After separation, the solvent was washed with water (100 ml), 5% w/v sodium bicarbonate solution (100 ml) and water (100 ml). The solvent was removed in vacuo to give the title compound (11.4 g).

IR and NMR data confirmed the structure as that of the title product, containing only 30% of the original phenoxyacetic acid as impurity.

EXAMPLE 20

N-(2,2,2-Trichloroethoxycarbonyl)glutamic acid bis diphenylmethyl ester 2,2,2-Trichloroethyl chloroformate (5.5 ml, 40 mM) was added to a solution of DL-glutamic acid (3.38 g, 20 mM) in water (100 ml). The solution pH was maintained at 7.5 – 8.0 for 30 minutes using 10% w/v sodium hydroxide solution. The solution was then extracted with dichloromethane (2 × 100 ml) at pH 5.0. A solution of diphenyldiazomethane (85 g, 44 mM) in dichloromethane (140 ml) was added to the aqueous phase and the pH adjusted to 2.0 using 10% v/v sulphuric acid over 15 minutes. After separation, the solvent was washed with water (3 × 150 ml). The solvent was removed in vacuo to give the title compound (14.3 g).

IR and NMR data confirmed the structure as that of the title compound.

EXAMPLE 21

N-Benzyloxycarbonylglycine bis diphenylmethyl ester

A solution of diphenyldiazomethane (2.1 g, 11 mM) in dichloromethane (32 ml) was added to a solution of N-benzyloxycarbonyl glycine (2.1 g, 10 mM) in water (50 ml.). The pH was adjusted to 3.5 using 10% v/v sulphuric acid over 15 minutes. After separation, the solvent was washed with water (3 × 50 ml), then removed in vacuo. The product was then precipitated by the addition of excess ether. The precipitate was filtered and washed with ether (15 ml) to give the title compound (3.4 g).

IR and NMR data confirmed the structure as that of the title compound.

EXAMPLE 22

N-(2,2,2-Trichloroethoxycarbonyl) glutathione bis diphenylmethyl ester

The process of Example 13 was repeated, except that glutathione (6.14 g, 20 mM) was treated in place of potassium (6R,7R)-7-(R-5-amino-5-carboxypentanamido)-3-hydroxymethylceph-3-em-4-carboxylate, to give the title compound (11.3 g).

IR and NMR data confirmed the structure as that of the title compound.

EXAMPLE 23

DL- Methionine diphenylmethylester, p-toluene sulphonic acid salt

D,L-Methionine (3.0 g, 20 mM) and p-toluene sulphonic acid monohydrate (3.8 g, 20 mM) were dissolved in water (50 ml) at ambient temperature. Dichloromethane (50 ml) containing diphenyldiazomethane (4.85 g, 25 mM) was added and the mixture stirred for 1 hour at pH 2. After separation, the solvent layer was washed with 5% sodium bicarbonate solution (50 ml) and water (50 ml). The solvent was removed in vacuo and the product crystallised from acetonitrile. Filtration and washing with acetonitrile (15 ml) gave the title compound (5.4 g).

The melting point and IR and NMR data confirmed the structure as that of the title compound.

EXAMPLE 24

Diphenylmethyl (6R,7R)-7-amino-3-acetoxymethylceph-3-em-4-carboxylate hydrochloride 2,2,2-Trichloroethyl chloroformate (4.2 ml, 31mM) was added to an aqueous solution (100 ml) containing the potassium salts of (6R,7R)-7-(R-5-amino-5-carboxypentanamido)-3-acetoxymethylceph-3-em-4-carboxylic acid (10 mM) and (6R,7R)-7-(R-5-amino-5-carboxypentanamido)-3-hydroxymethylceph-3-em-4-carboxylic acid (10 mM).

The solution pH was maintained at 7.5 – 8.0 for 1 hour using 10% w/v sodium hydroxide solution. The solution was then extracted with dichloromethane (50 ml) at pH 5.0. A solution of diphenyldiazomethane (8.5 g, 44 mM) in dichloromethane (150 ml) was added to the aqueous phase and the pH adjusted to 3.5 using 10% v/v sulphuric acid over 30 minutes. After separation the solvent was washed with water (3 × 150 ml) and stirred with anhydrous magnesium sulphate (10 g). After filtering off the solid the solution was concentrated by distillation in vacuo to 50 ml. Acetyl chloride (4.3 ml, 60 mM) and pyridine (4.8 ml, 60 mM) were added to the solution with cooling to maintain a temperature of 5°-10°. After stirring for 30 minutes the solution was filtered and added to a slurry of phosphorus pentachloride (9.0 g, 43 mM) and pyridine (3.5 ml, 43 mM) in dichloromethane (40 ml). During the addition the temperature was maintained at −5°. The mixture was stirred for 50 minutes maintaining the temperature between 0° and 5°. After cooling to −10° methanol (40 ml) was added and stirring was continued for a further 15 minutes. Water (40 ml) and di-isopropyl ether (250 ml) were then added and the product allowed to crystallise for 1 hour. The product was filtered, washed with a mixture of methanol and di-isopropyl ether (30:70, 100 ml) and dried in vacuo to give the title compound (7.8 g).

IR and NMR data confirmed the structure as that of the title compound.

We claim:

1. In a process for extracting an N-blocked amino acid from a fermentation broth or other aqueous solutions wherein the improvement comprises treating a fermentation broth or other predominantly aqueous solutions containing an N-blocked amino acid with a diazoalkane in the presence of a water immiscible organic solvent to substantially simultaneously esterify said N-blocked amino acid and produce a solution of the thus formed ester in said water immiscible organic solvent.

2. The process of claim 1 wherein said diazoalkane is diphenyldiazomethane.

3. The process of claim 1 wherein said aqueous solution of the N-blocked amino acid is a whole or filtered fermentation broth.

4. The process of claim 1 wherein the N-blocked amino acid is a naturally occuring penicillin or cephalosporin compound in which any free amino groups have been blocked.

5. The precess of claim 4 wherein the N-blocked amino acid is an N-blocked derivative of desacetyl cephalosporin C.

6. The process of claim 4 wherein the N-blocked amino acid is a mixture of N-blocked derivatives of cephalosporin C and desacetyl cephalosporin C.

7. The process of claim 1 wherein the N-blocked amino acid is an N-blocked derivative of glutathione.

8. The process of claim 1 wherein the diazoalkane is added in solution in the organic solvent to the aqueous solution of the N-blocked amino acid.

9. The process of claim 1 wherein the extractive esterification is effected by reducing the pH of a neutral or basic solution of the N-blocked amino acid using a strong acid having a pKa less than that of the N-blocked amino acid, after addition of the diazoalkane and water-immiscible organic solvent.

10. The process of claim 1 wherein the N-blocked amino acid is an amine N-blocked compound selected from the group consisting of naturally occurring amino acids in which the amino group or groups are blocked, peptides in which the amino group or groups are blocked, β-lactam compounds of the penicillin and cephalosporin series in which any free amino groups are blocked, penilloic acid and penicilloic acid.

11. The process of claim 1 wherein the N-blocked amino acid is selected from the group consisting of glycine, cysteine, methionine, aspartic acid, glutamic acid, phenylalanine, tryptophane and L-dopa.

12. The process of claim 1 wherein the water-immiscible organic solvent is selected from the group consisting of chlorinated hydrocarbons, aliphatic esters, aromatic esters, ketones, aliphatic hydrocarbons, aromatic hydrocarbons and mixtures thereof.

13. The process of claim 1 wherein the water-immiscible organic solvent is selected from the group consisting of methylene chloride, chloroform, chlorobenzene, ethyl acetate, butyl acetate, ethyl benzoate, methyl ethyl ketone, methyl isobutyl ketone, benzene, n-butanol and mixtures thereof.

14. The process of claim 1 wherein the pH of the fermentation broth or other aqueous solutions is in the range of 2.0–4.0.

* * * * *